US012758803B2

(12) United States Patent
Jang

(10) Patent No.: US 12,758,803 B2
(45) Date of Patent: Oct. 13, 2026

(54) LIFTING BEAUTY DEVICE USING HIGH-INTENSITY FOCUSED ULTRASOUND

(71) Applicant: Wooahan Inc., Ansan-si (KR)

(72) Inventor: Daekyu Jang, Hwaseong-si (KR)

(73) Assignee: Wooahan Inc., Ansan-si (KR)

( * ) Notice: Subject to any disclaimer, the term of this patent is extended or adjusted under 35 U.S.C. 154(b) by 0 days.

(21) Appl. No.: 19/116,436

(22) PCT Filed: Oct. 4, 2023

(86) PCT No.: PCT/KR2023/015256

§ 371 (c)(1),
(2) Date: Apr. 23, 2025

(87) PCT Pub. No.: WO2024/072192

PCT Pub. Date: Apr. 4, 2024

(65) Prior Publication Data

US 2025/0256133 A1 Aug. 14, 2025

(30) Foreign Application Priority Data

Sep. 30, 2022 (KR) ........................ 10-2022-0125602
Dec. 8, 2022 (KR) ........................ 10-2022-0170832

(51) Int. Cl.
*A61N 7/02* (2006.01)
*A61N 7/00* (2006.01)

(52) U.S. Cl.
CPC ........ *A61N 7/02* (2013.01); *A61N 2007/0034* (2013.01)

(58) Field of Classification Search
CPC .... A61N 2007/0034; A61N 2007/0008; A61N 2007/0091
See application file for complete search history.

(56) References Cited

U.S. PATENT DOCUMENTS

2017/0303895 A1* 10/2017 Park ........................ A61N 7/02

FOREIGN PATENT DOCUMENTS

KR 10-1335476 B1 12/2013
KR 10-2018-0015095 A 2/2018
(Continued)

OTHER PUBLICATIONS

International Search Report for PCT/KR2023/015256 mailed Feb. 2, 2024 from Korean Intellectual Property Office.

*Primary Examiner* — Jason M Ip
(74) *Attorney, Agent, or Firm* — Revolution IP, PLLC

(57) ABSTRACT

The present invention provides a lifting beauty device using high-intensity focused ultrasound that includes a body portion having a circumference gripped by a hand of a user and configured to generate a rotational power as the user operates an operation button exposed on a surface, and a cartridge portion that is coupled to a front side of the body portion and emits high intensity focused ultrasound (HIFU) while moving along a corresponding path by the rotational power generated by the body portion and selectively switching an emission depth in two stages depending on an operation mode, that may selectively switch an emission depth of the high-intensity focused ultrasound (HIFU) such that the high-intensity focused ultrasound (HIFU) may selectively reach an SMAS (Superficial Musculo Aponeurotic System) layer, which is a fibrous fascia layer that is part of a muscle layer, or a dermis layer.

7 Claims, 7 Drawing Sheets

(56) References Cited

FOREIGN PATENT DOCUMENTS

| | | | |
|---|---|---|---|
| KR | 10-2018-0089309 | A | 8/2018 |
| KR | 10-2021-0000221 | A | 1/2021 |
| KR | 10-2256560 | B1 | 5/2021 |
| KR | 10-2021-0112226 | A | 9/2021 |

* cited by examiner

LIFTING BEAUTY DEVICE USING HIGH-INTENSITY FOCUSED ULTRASOUND

CROSS REFERENCE TO PRIOR APPLICATIONS

This application is a National Stage Application of PCT International Patent Application No. PCT/KR2023/015256 filed on Oct. 4, 2023, under 35 U.S.C. § 371, which claims priority to Korean Patent Application Nos. 10-2022-0125602 filed Sep. 30, 2022, and 10-2022-0170832 filed Dec. 8, 2022 which are all hereby incorporated by reference in their entirety.

TECHNICAL FIELD

The present invention relates to a lifting beauty device using high-intensity focused ultrasound, and more specifically, to a lifting beauty device using high-intensity focused ultrasound that may selectively switch an emission depth of the high-intensity focused ultrasound (HIFU) such that the high-intensity focused ultrasound (HIFU) may selectively reach an SMAS (Superficial Musculo Aponeurotic System) layer, which is a fibrous fascia layer that is part of a muscle layer, or a dermis layer.

BACKGROUND ART

In general, as many people begins to take an interest in beauty, interest in skin beauty is also increasing day by day.

The desire for healthy skin is not limited to a beauty field, but also affects the growth of medical services to protect skin health from UV rays and various types of pollution that are becoming stronger due to the destruction of the ozone layer.

Face lifting is a wrinkle removal surgery that aims to improve the aging phenomenon of a facial area by removing sagging skin on the face and neck and pulling subcutaneous tissue to remove wrinkles.

Recently, endoscopic methods have been used to minimize scars by making fewer incisions during face lifting.

However, because the methods are invasive surgical procedures, the methods cause many difficulties for persons who undergo the procedure due to bleeding, secondary infections, pain, and long recovery periods.

Among invasive methods, advanced medical technologies such as lasers are being developed and commercialized, but there are still difficulties associated with invasive surgeries.

Therefore, the need for a technology that may beautify the skin in a non-invasive way has been increasing recently.

In general, the SMAS layer, which is part of a muscle layer, is a muscle area that is pulled when performing a face lifting surgery, and clinical results have been reported overseas that, when high-intensity focused ultrasound is used to only act on the SMAS layer without touching the epidermis, the heat from the ultrasound is transferred to a deep portion of the dermis layer, which regenerates collagen and achieves an effect of removing wrinkles and increasing skin elasticity.

In line with this trend, there is a beauty device that uses high intensity focused ultrasound (HIFU), which is a non-invasive beauty device that has recently been in the spotlight.

There is an ultrasonic beauty device that emits high intensity focused ultrasound to shallow skin tissues for skin beauty treatment to perform skin lifting or skin tightening treatment, and the ultrasonic beauty device emits the high intensity focused ultrasound (HIFU) to a subcutaneous fat layer, a dermis layer, and so on and stimulates while burning or melting and decomposing the subcutaneous biological tissues, and accordingly, wrinkles are removed, and skin elasticity is improved.

The related art includes Korean Patent No. 10-1335476 (2013 Nov. 26).

DISCLOSURE OF INVENTION

Technical Problem

The present invention aims to provide a lifting beauty device using high-intensity focused ultrasound, which may emit high-intensity focused ultrasound (HIFU) at two emission depths (4.5 mm and 3.0 mm), such that the high-intensity focused ultrasound (HIFU) may reach a SMAS (Superficial Musculo Aponeurotic System) layer which is a fibrous fascia layer that is part of a muscle layer, or a dermis layer, thereby regenerating collagen to obtain an effect of removing wrinkles and increasing skin elasticity.

Solution to Problem

According to the present invention, a lifting beauty device using high-intensity focused ultrasound includes a body portion having a circumference gripped by a hand of a user and configured to generate a rotational power as the user operates an operation button exposed on a surface; and a cartridge portion coupled to an upper side of the body portion and having an ultrasound emission head that emits high intensity focused ultrasound (HIFU) with the rotational power generated by the body portion and emits the high-intensity focused ultrasound (HIFU) in two emission depths while moving along a corresponding path.

At this time, the body portion according to the present invention includes a body housing that has an internal space having an internal length from top to bottom and includes a plurality of operation buttons on a surface, a battery accommodated on the lower side of the internal space of the body housing and electrically connected to an external power source and an input terminal to be charged with electricity, and outputting the charged electricity through an output terminal, an electric motor accommodated on an upper side of the internal space of the body housing, electrically connected to the output terminal of the battery, and causing a motor gear, which is rotatably provided on an upper side of the body housing, to rotate, and a control board provided in the internal space of the body housing, electrically connected to the electric motor and the battery, and controlling a power output of the battery based on a signal input through the operation button to control operations of the electric motor and the cartridge portion.

Here, according to the present invention, the lifting beauty device further include a coupling portion which is formed on the upper side of the body housing and into which a lower end of the cartridge portion is inserted, and a pair of connection terminals which are spaced apart from the motor gear located at an inner center of the coupling portion by a certain distance and are electrically connected to the control board, and from which power is output to the cartridge portion through the control board.

In addition, the cartridge portion according to the present invention includes a cartridge housing having an internal space, including an insertion portion inserted into the coupling portion, and having an oval-shaped opening formed in an upper side through which an ultrasonic oscillation head is movable, a rotational power transfer means accommodated on a lower side inside the cartridge housing and receiving and outputting a rotational power generated by the body portion, a head transport means mechanically connected to the rotational power transfer means in the internal space of the cartridge housing and linearly transporting the head module with the rotational power output from the rotational power transfer means, and the head module connected to the head transport means in the internal space of the cartridge housing and emitting the high-intensity focused ultrasound (HIFU) while linearly moving by the head transport means.

At this time, the rotational power transfer means according to the present invention includes a connection gear that is engaged with the motor gear, and a first bevel gear connected to the connection gear by an axis to rotate in conjunction with a rotation of the connection gear.

Also, the head transport means according to the present invention includes a rotation shaft having a second bevel gear, which is engaged perpendicularly with the first bevel gear, on one side and having a first spur gear on an opposite side of the one side, and a transfer screw having a length that is parallel to the rotation axis and a screw thread formed in the length, and having a second spur gear, which is engaged with the first spur gear, on another side.

In addition, the head module according to the present invention includes a first head holder provided on the transfer screw and moving linearly in response to an axial rotation of the transfer screw, a second head holder coupled to an upper side of the first head holder and including an ultrasonic oscillation head that emits the high intensity focused ultrasound (HIFU), a guide pin rotatably provided on the second head holder and including semicircular guides formed on both ends, and a guide plate arranged orthogonally to a longitudinal direction of the guide pin and having a track groove that guides a guide of the guide pin along a corresponding path.

In addition, the track home of the guide plate according to the present invention includes a first high-intensity focused ultrasound emission section that limits an emission depth of the focused ultrasound to 3.0 mm, a second high-intensity focused ultrasound emission section that limits the emission depth of the focused ultrasound to 4.5 mm, and a pair of emission depth switching sections connecting one side and another side of the first high-intensity focused ultrasound emission section respectively to one side and another side of the second high-intensity focused ultrasound emission section.

Advantageous Effects of Invention

Effects of a lifting beauty device using high-intensity focused ultrasound according to the present invention are as follows.

High-intensity focused ultrasound (HIFU) may be emitted at two emission depths (4.5 mm and 3.0 mm), such that the high-intensity focused ultrasound (HIFU) reaches a SMAS (Superficial Musculo Aponeurotic System) layer, which is a fibrous fascia layer that is part of a muscle layer, or a dermis layer, and thus, collagen is regenerated, and thereby, an effect of wrinkle removal and increased skin elasticity may be obtained.

Also, the emission depth of the high-intensity focused ultrasound (HIFU) may be selectively switched, and thus, the replacement of an ultrasound emission plug is not necessary, which may reduce the treatment time and reduce the fatigue of an operator.

BEST MODE FOR CARRYING OUT THE INVENTION

Figure 1:
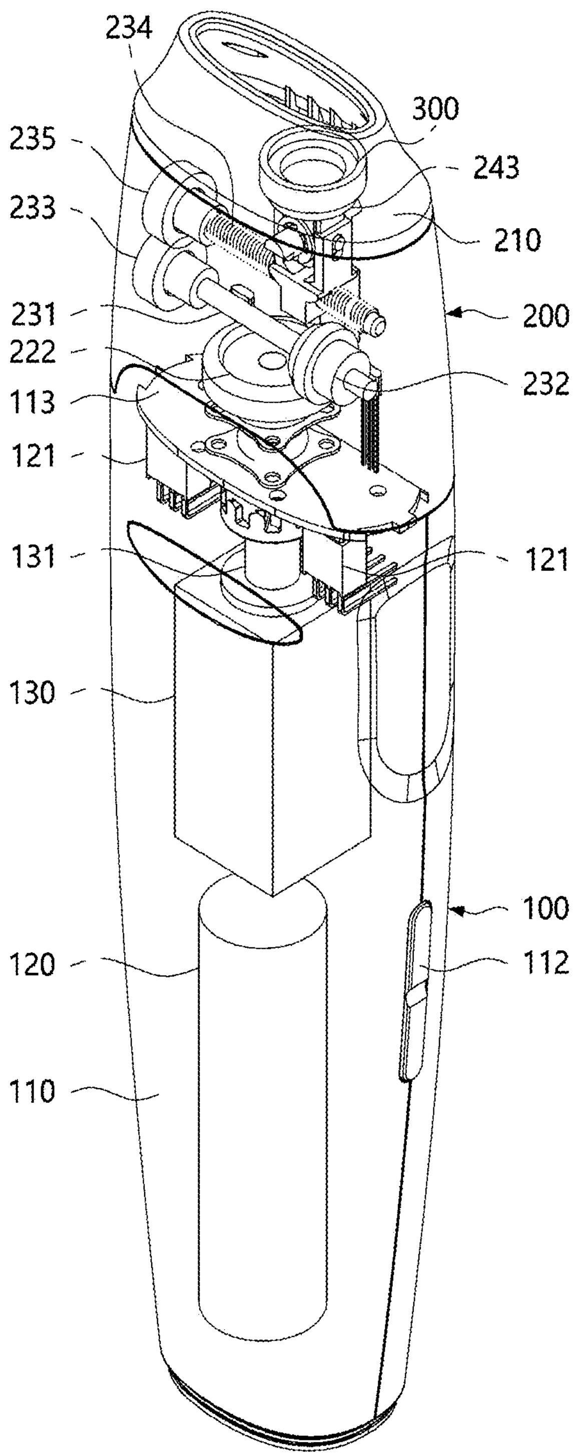
FIG. 1 is a perspective view illustrating a lifting beauty device using high-intensity focused ultrasound, according to an embodiment of the present invention.
Figure 2:
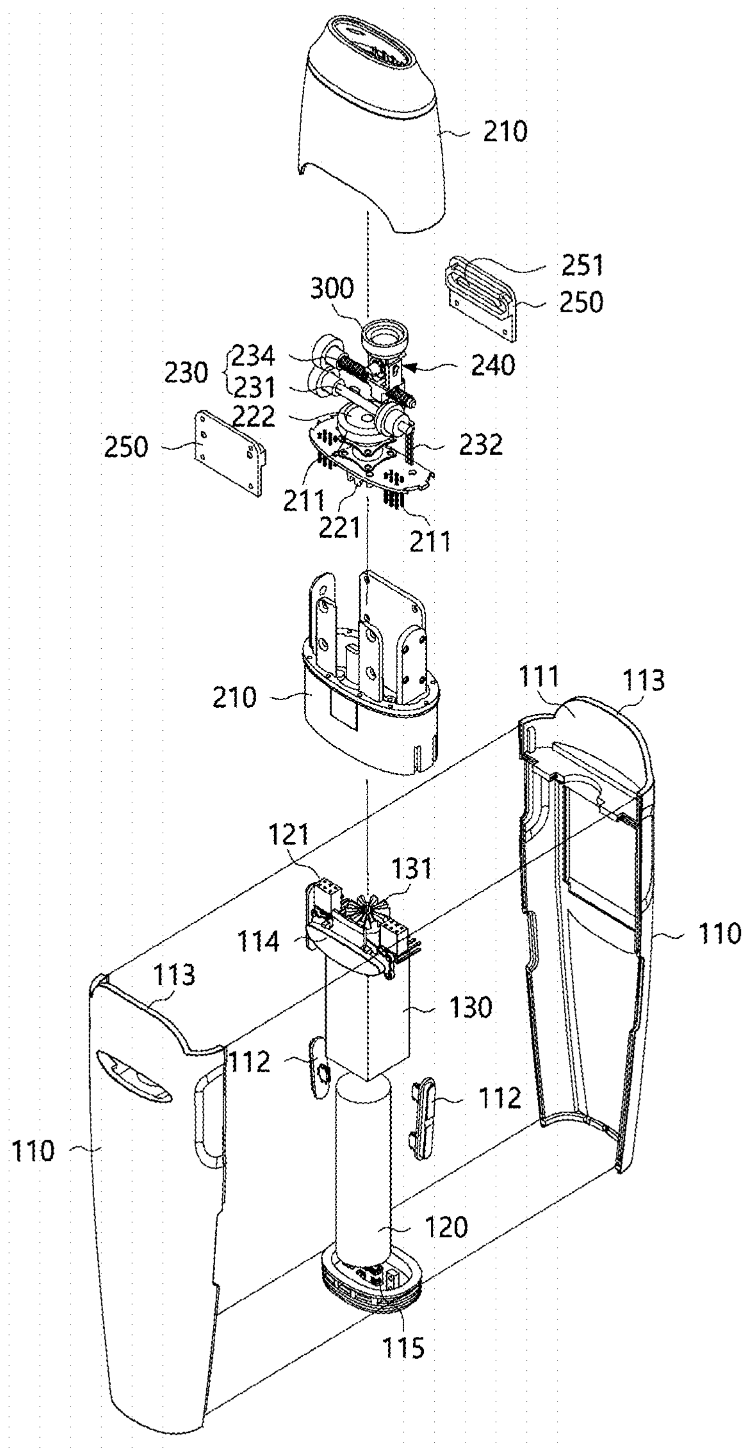
FIG. 2 is an exploded perspective view illustrating a configuration of a body portion and a cartridge portion according to an embodiment of the present invention.
Figure 3:
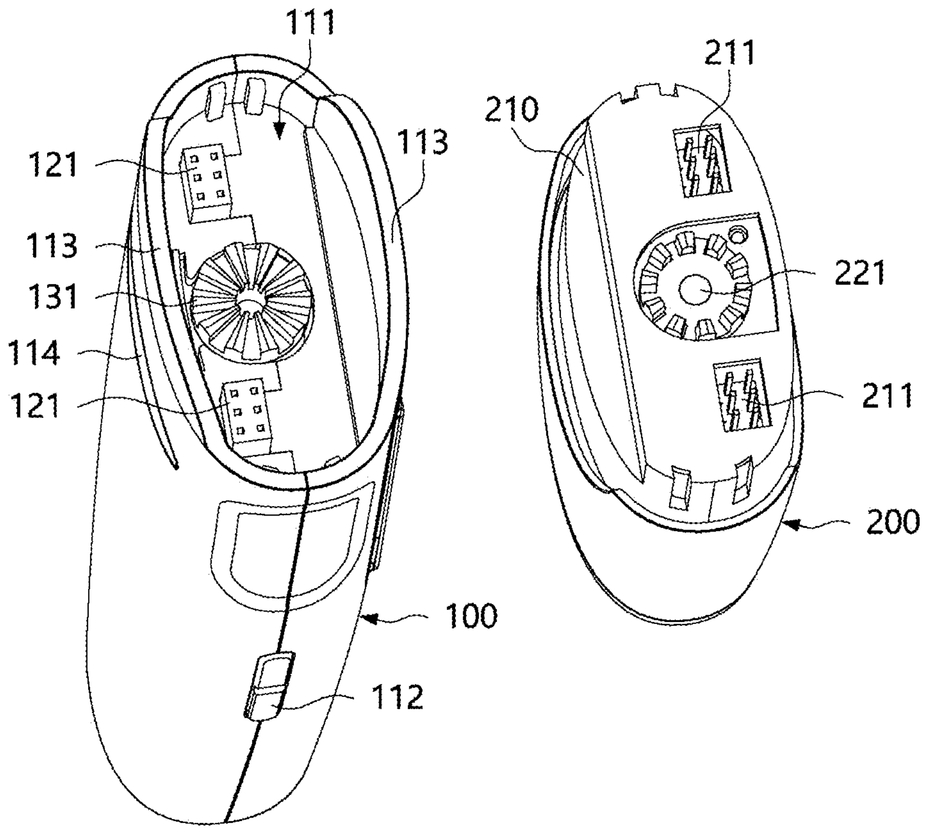
FIG. 3 is a view illustrating a state in which a cartridge portion is separated from a body portion according to an embodiment of the present invention.

The present invention provides a lifting beauty device using high-intensity focused ultrasound including a body portion having a circumference gripped by a hand of a user and configured to generate a rotational power as the user operates an operation button exposed on a surface; and a cartridge portion coupled to an upper side of the body portion and having an ultrasound emission head that emits high intensity focused ultrasound (HIFU) with the rotational power generated by the body portion and emits the high-intensity focused ultrasound (HIFU) in two emission depths while moving along a corresponding path, wherein the head module according to the present invention includes a first head holder provided on the transfer screw and moving linearly in response to an axial rotation of the transfer screw, a second head holder coupled to an upper side of the first head holder and including an ultrasonic oscillation head that emits the high intensity focused ultrasound (HIFU), a guide pin rotatably provided on the second head holder and including semicircular guides formed on both ends, and a guide plate arranged orthogonally to a longitudinal direction of the guide pin and having a track groove that guides a guide of the guide pin along a corresponding path, and the track home of the guide plate according to the present invention includes a first high-intensity focused ultrasound emission section that limits an emission depth of the focused ultrasound to 3.0 mm, a second high-intensity focused ultrasound emission section that limits the emission depth of the focused ultrasound to 4.5 mm, and a pair of emission depth switching sections connecting one side and another side of the first high-intensity focused ultrasound emission section respectively to one side and another side of the second high-intensity focused ultrasound emission section.

Mode for Carrying Out the Invention

Hereinafter, preferred embodiments according to the present invention will be described in detail with reference to the attached drawings. Prior to this, the terms or words used in the present specification and claims should not be interpreted as limited to their usual or dictionary meanings, and should be interpreted as meanings and concepts that conform to the technical idea of the present invention based on a principle that the inventor may appropriately define concepts of the terms in order to describe his or her own invention in the best way.

Therefore, the embodiments described in the present specification and configurations illustrated in the drawings are only the most preferred embodiments of the present invention, and do not represent all of the technical ideas of the present invention, and accordingly, it should be understood that there may be equivalent modification examples that may be replaced at the time of this application.

The present invention relates to a lifting beauty device using high-intensity focused ultrasound, which may selectively switch an emission depth of the high-intensity focused ultrasound (HIFU) such that high-intensity focused ultrasound (HIFU) may selectively reach an SMAS (Superficial Musculo Aponeurotic System) layer, which is a fibrous fascia layer that is part of a muscle layer, or a dermis layer, and is described below with reference to the drawings.

A lifting beauty device using high-intensity focused ultrasound according to an embodiment of the present invention to be described with reference to FIGS. 1 to 7 includes a body portion 100 and a cartridge portion 200, and an entire shape of the ultrasonic lifting beauty device is a streamline shape, the cartridge portion 200 is located at an upper part, and the body portion 100 is located at a lower part of the cartridge portion 200.

Accordingly, a user holds the body portion 100 with his/her hand, and moves the lifting beauty device along a skin line while a front surface of the cartridge portion 200 is in contact with the skin, and performs a lifting procedure by causing high-intensity focused ultrasound (HIFU) to be emitted to an SMAS (Superficial Musculo Aponeurotic System) layer, which is a fibrous fascia layer that is part of the muscle layer, or a deep part of a dermis layer.

Here, the body portion 100 and the cartridge portion 200 according to one embodiment of the present invention are described in detail below.

First, as the body portion 100 is gripped by a user's hand around a circumference thereof and a user operates multiple operation buttons 112 exposed on a surface, the body portion 100 generates a power output and rotational power that may drive the cartridge portion 200.

At this time, the body portion 100 includes a body housing 110, a battery 120, and an electric motor 130, and the body housing 110 forms an internal space, and the battery 120 and the electric motor 130 are built in the internal space.

Here, a coupling portion 111 is formed on an upper side of the body housing 110 which a lower side of the cartridge portion 200 is inserted into to be connected to, and a motor gear 131 that provides rotational power, which is a power for moving an ultrasonic oscillation head 300 equipped in the cartridge portion 200, is provided at an internal center of the coupling portion 111, and a pair of terminals 121 are provided on the left and right sides of the motor gear 131 to supply power for driving the ultrasonic oscillation head 300.

Also, support pieces 113 are formed to extend in an arc shape respectively from upper left and right sides of the coupling portion 111 toward the cartridge portion 200, and the support pieces 113 support the cartridge portion 200 coupled to the coupling portion 111 so as not to be separated from the coupling portion 111 by a physical force applied from a side of the cartridge portion 200.

In addition, it is preferable that the coupling portion 111 further includes a catch means 114 that prevents the cartridge portion 200 inserted in the coupling portion 111 from being easily separated.

The catch means 114 is supported by an elastic body (not illustrated) and connected to a push button formed on a surface of the body housing 110, such that the cartridge portion 200 is released from engagement by moving forward and backward by a forward and backward force applied through the push button.

In addition, the battery 120 built on a lower side in an internal space of the body housing 110 selectively supplies power to the electric motor 130 and the cartridge portion 200, and is preferably configured with a rechargeable battery that is charged with electricity.

At this time, the battery 120 is electrically connected to the charging terminal 115 provided at a lower portion of the body housing 110 and is connected to an external power source through the charging terminal 115 to charge electricity.

Also, the battery 120 is electrically connected to a control board (not illustrated) built in the body housing 110, and the control board is electrically connected to an operation button 112 to control power supplied to the electric motor 130 and the cartridge portion 200 according to on/off of a device, selection of an operation mode, selection of an emission depth, and so on.

In addition, the battery 120 is electrically connected to the pair of terminals 121 provided in the coupling portion 111 through the control board, and supplies power to the ultrasonic oscillation head 300 provided in the cartridge portion 200.

In addition, the electric motor 130 built in an upper portion of the internal space of the body housing 110 is electrically connected to the battery 120 and the control board like a normal electric motor, and generates a rotational power of forward or reverse rotation with the power supplied from the battery 120 under the control by the control board.

At this time, a rotational axis of the electric motor 130 is coupled to the motor gear 131 located in the center of the coupling portion 111 of the body housing 110, and the motor gear 131 is a crown gear and rotates forward or reversely in conjunction with the rotational axis of the electric motor 130.

The cartridge portion 200 is connected to the coupling portion 111 of the body portion 100, and selectively switches an emission depth in two stages and emits high intensity focused ultrasound (HIFU) using the power generated by the body portion 100.

Here, in more detail, the cartridge portion 200 according to one embodiment of the present invention includes a cartridge housing 210, a rotational power transfer means 220, a head transport means 230, and a head module 240.

First, the cartridge housing 210 forms an internal space, and the rotational power transfer means 220, the head transport means 230, the head module 240, and a guide member 250 are built in the internal space.

Figure 4:
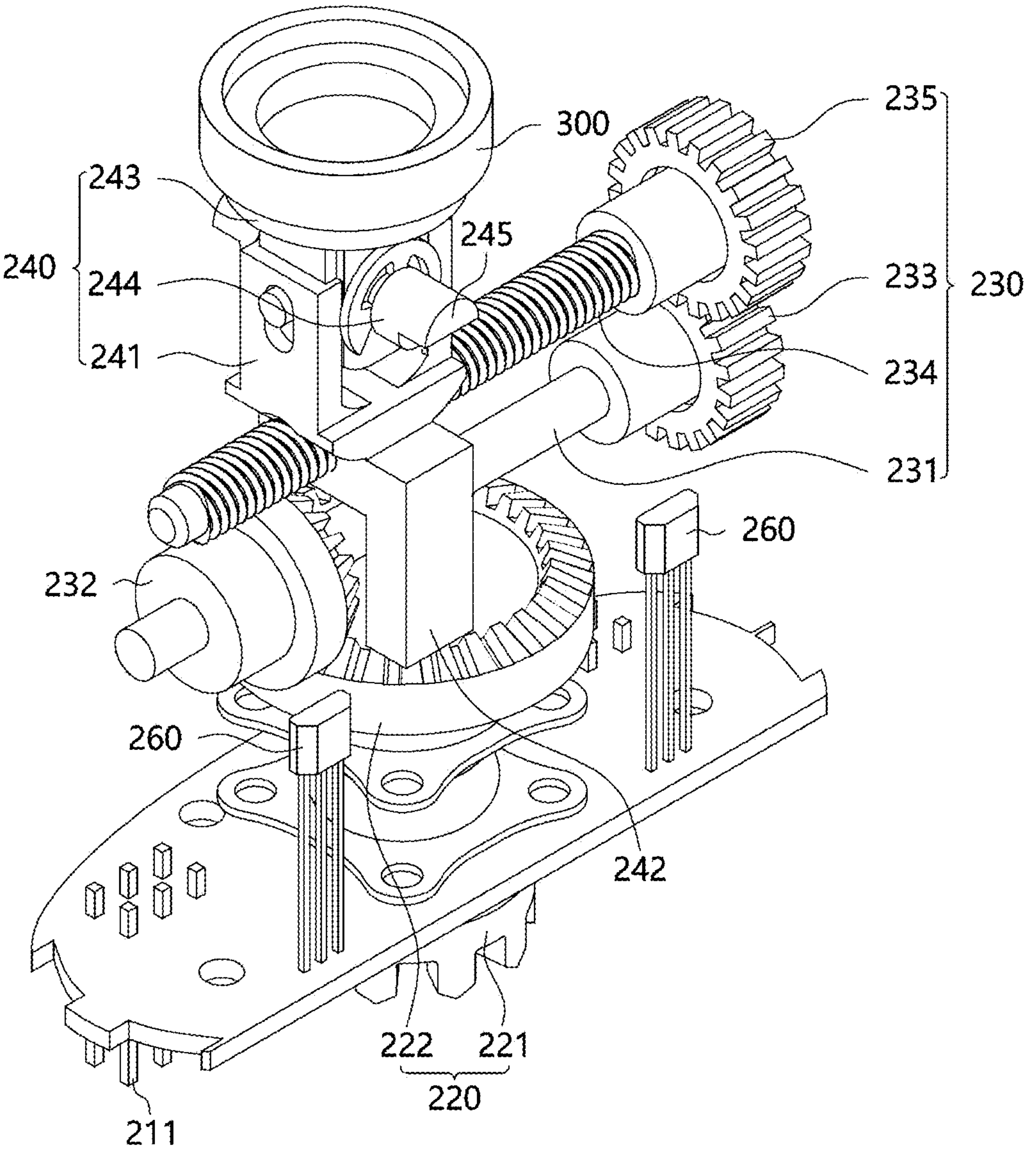
FIG. 4 is a view illustrating a rotational power transfer means, a head transport means, and a head module of a cartridge portion according to an embodiment of the present invention.
Figure 5:
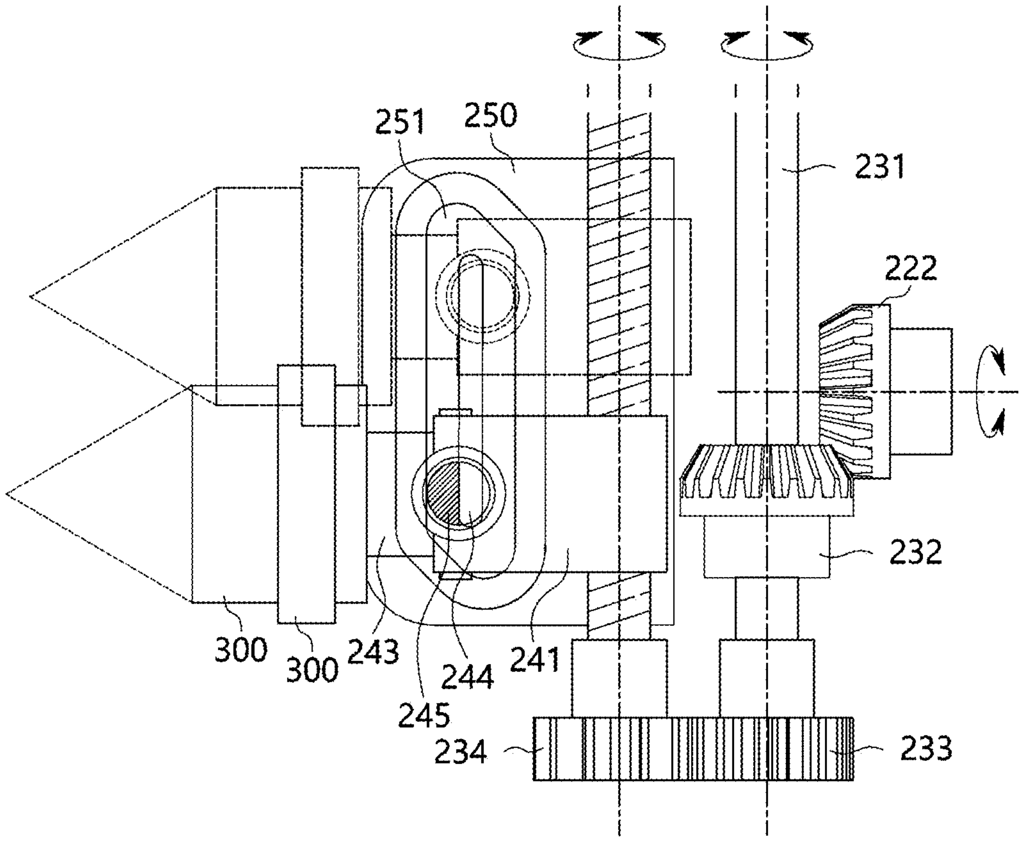
FIG. 5 is a view illustrating movement of a head module according to an embodiment of the present invention.
Figure 6:
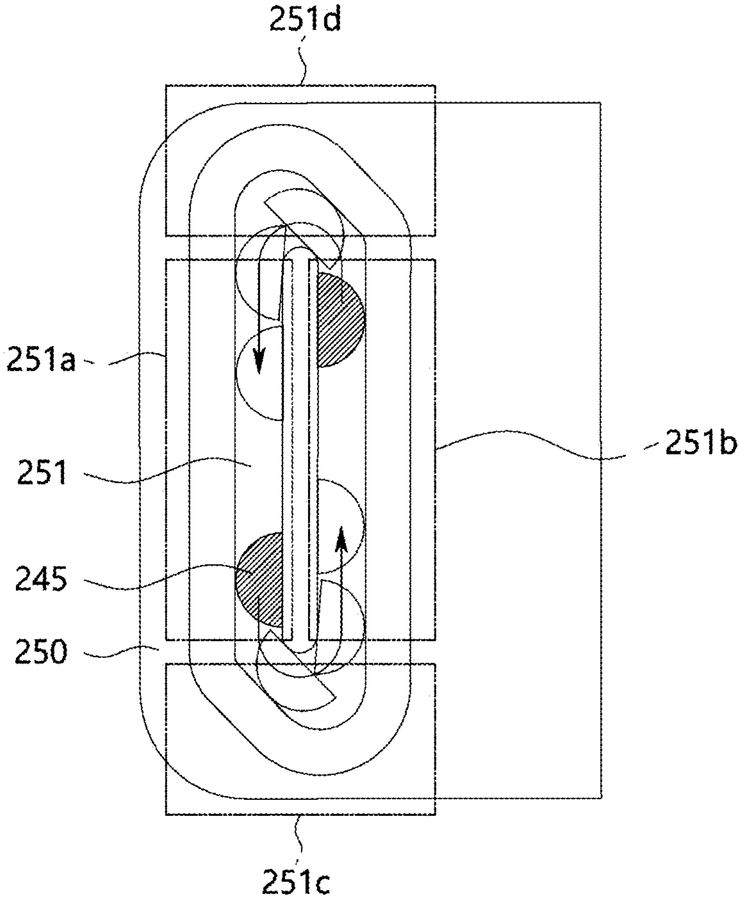
FIG. 6 is a view illustrating a state in which a guide of a head module is switched, according to an embodiment of the present invention.
Figure 7:
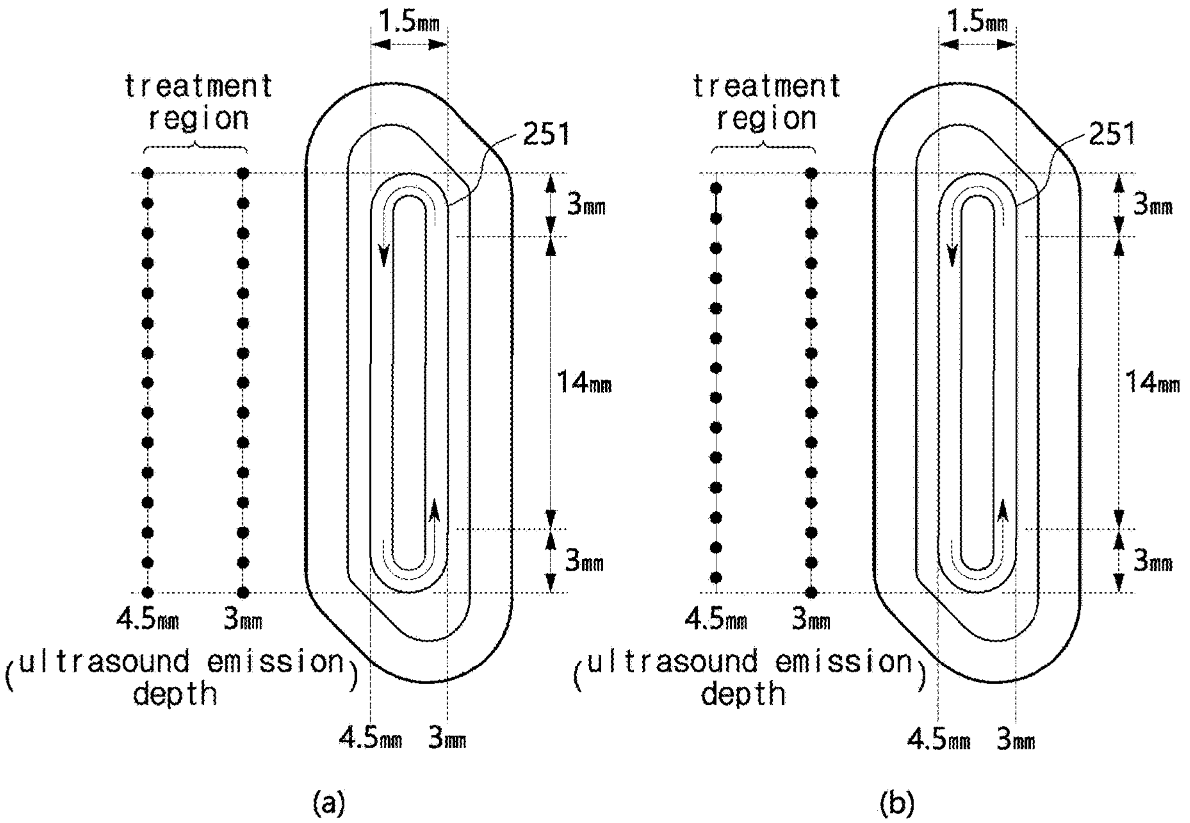
FIG. 7 illustrates views of states in which a lifting beauty device using high-intensity focused ultrasound according to an embodiment of the present invention emits high-intensity focused ultrasound.

Referring to FIGS. 4 and 5, the rotational power transfer means 220 transfers the rotational power generated by the electric motor 130 of the body portion 100 to the head transport means 230, and includes a connection gear 221, which is engaged with the motor gear 131, and a first bevel gear 222 that is axially connected to the connection gear 221.

At this time, it is preferable that the connection gear 221 is also formed as a crown gear so as to be able to be engaged with the motor gear 131, and a shaft connecting the connection gear 221 to the first bevel gear 222 is fixed with a bearing or so on so as to be able to rotate in the cartridge housing 210.

Therefore, the rotational power transfer means 220 receives the rotational power generated by the electric motor 130 of the body portion 100 through the connection gear 221 and outputs the rotational power to the first bevel gear 222 connected to the connection gear 221 by an axis.

Here, a pair of connecting pins 211 are provided at a lower portion of the cartridge housing 210 at positions corresponding to the pair of terminal terminals 121 centered on the connection gear 221 of the rotational power transfer means 220, and the connecting pins 211 are electrically connected to the ultrasonic oscillating head 300, and when the cartridge portion 200 is connected to the connecting portion 111 of the body portion 100, the cartridge portion 200 may each be inserted into the terminal terminals 121 and electrically connected thereto.

Accordingly, electricity is supplied to the ultrasonic oscillation head 300 provided in the cartridge portion 200 by a connection between a terminal 121 and the connection pin 211.

In addition, the head transport means 230 is mechanically connected to the rotational power transfer means 220 to linearly transfer the head module 240.

The head transport means 230 includes a rotational shaft 231 and a transfer screw 234 of which axes are parallel to each other, and a second bevel gear 232 is provided on one side of the rotational shaft 231 so as to be engaged with the first bevel gear 222 of the rotational power transfer means 220 at right angles to switch a rotational direction to be orthogonal, and a first spur gear 233 is provided on the other side of the rotational shaft 231 such that the first spur gear 233 also rotates due to the axial rotation of the rotational shaft 231.

A second spur gear 235, which is engaged with the first spur gear 233, is provided on the other side of the transfer screw 234 provided to be parallel to the rotational shaft 231 such that the rotational shaft 231 is rotated by the rotational power transferred through the second bevel gear 232 engaged with the first bevel gear 222 of the rotational power transfer means 220, and when the first spur gear 233 rotates due to the rotation of the rotational shaft 231, the engaged second spur gear 235 rotates, causing the feed screw 234 to rotate, and thus the head module 240 connected to the feed screw 234 is linearly transported.

The head module 240 includes a first head holder 241 that is coupled to the feed screw 234 and moves in an axial direction of the feed screw 234 according to the rotation of the feed screw 234.

At this time, the first head holder 241 has a 'U' shape, and a cam block 242 is formed to extend from a lower side of the first head holder 241, and the cam block 242 may check a position of the ultrasonic oscillation head 300 in correspondence with a pair of position sensors 260 arranged on one end and the other end of the transfer screw 234.

In addition, a second head holder 243 is coupled to an upper side of the first head holder 241, and the second head holder 243 has the ultrasonic oscillation head 300 mounted on a front end thereof, and is coupled between upper portions of the first head holder 241 forming a 'U' shape.

At this time, coupling protrusions are respectively formed on the left and right sides of the second head holder 243, and coupling holes, into which the coupling protrusions are respectively inserted, are formed in the first head holder 241, and the coupling holes are formed as long holes each having a length from top to bottom, and accordingly, the second head holder 243 may move as much as a length of the coupling hole on an upper side of the first head holder 241.

Referring to FIG. 4 to FIG. 7, the second head holder 243 includes a guide rotation pin 244, and the guide rotation pin 244 is provided to be rotatable in the second head holder 243, and a guide 245 having a semicircular cross-section is formed at both ends.

At this time, the guide 245 of the guide rotation pin 244 corresponds to a pair of guide plates 250 provided at the front and rear of the head module 240, and a track groove 251 that guides the guide 245 of the guide rotation pin 244 is formed in the guide plate 250.

It is preferable that the track groove 251 is formed into an elliptical shape by combining the first and second high-intensity focused ultrasonic emission portions **251*a* and 251*b* and emission depth transition portions 251*c* and 251*d* on the left and right sides, and the internal side of the track groove 251 is in close contact with a flat surface of the semicircular guide 245, and an outer side of the track groove 251 is in close contact with the curved portion of the guide 245**.

Here, a first high-intensity focused ultrasound emission section **251*a* and a second high-intensity focused ultrasound emission section 251*b* are sections in which the ultrasonic oscillation head 300 coupled to the second head holder 243 emits high-intensity focused ultrasound (HIFU), and it is preferable that the first high-intensity focused ultrasound emission section 251*a* and the second high-intensity focused ultrasound emission section 251*b* are straight sections that are parallel to each other, and it is preferable that the first high-intensity focused ultrasound emission section 251*a*** limits an emission depth of the focused ultrasound to 3.0 mm, and the second high-intensity focused ultrasound emission section limits an emission depth of the focused ultrasound to 4.5 mm.

Therefore, according to an embodiment of the present invention, a lifting beauty device using high-intensity focused ultrasound has two emission depths of focused ultrasounds, 4.5 mm and 3.0 mm, such that high-intensity focused ultrasounds may be respectively and selectively emitted to the SMAS (Superficial Musculo Aponeurotic System) layer which is a fibrous fascia layer and a dermis layer, or the high-intensity focused ultrasound may be emitted to both the SMAS (Superficial Musculo Aponeurotic System) layer and the dermis layer.

In addition, emission depth switching section **251*c* and 251*d* where emission depths are switched is formed by including a straight path and a curved path such that the guide 245 may rotate along the track groove 251**.

Therefore, it is preferable that the guide 245 moving along a track home 251 moves only in one direction along the track home 251.

The present invention is described with reference to the embodiments illustrated in the drawing, but the embodiments are merely examples, and those skilled in the art will understand that various modifications and equivalent other embodiments may be derived therefrom. Therefore, the true technical protection scope of the present invention should be determined by the technical idea of the attached patent claims.

The invention claimed is:

1. A lifting beauty device using high-intensity focused ultrasound, the lifting beauty device comprising:

a body portion having a circumference gripped by a hand of a user and configured to generate a rotational power as the user operates an operation button exposed on a surface; and a cartridge portion coupled to an upper side of the body portion and having an ultrasonic oscillation head that emits high intensity focused ultrasound (HIFU) with the rotational power generated by the body portion and emits the high-intensity focused ultrasound (HIFU) in two emission depths while moving along a corresponding path, wherein the cartridge portion includes a head module, and the head module includes:

a first head holder provided on a transfer screw in the cartridge portion and moving linearly in response to an axial rotation of the transfer screw, the transfer screw being rotated with the rotational power generated by the body portion;

a second head holder coupled to an upper side of the first head holder, the second head holder including the ultrasonic oscillation head;

a guide pin rotatably provided on the second head holder, the guide pin including semicircular guides formed on both ends of the guide pin; and a guide plate arranged orthogonally to a longitudinal direction of the guide pin, the guide plate having a track groove that guides a guide of the guide pin along a path corresponding to the track groove such that the ultrasonic oscillation head emits the high-intensity focused ultrasound in the two emission depths.

2. The lifting beauty device using the high-intensity focused ultrasound of claim 1, wherein the body portion includes:

a body housing that has an internal space having an internal length from top to bottom and includes a plurality of operation buttons on a surface;

a battery accommodated on the lower side of the internal space of the body housing and electrically connected to an external power source and an input terminal to be charged with electricity, and outputting the charged electricity through an output terminal;

an electric motor accommodated on an upper side of the internal space of the body housing, electrically connected to the output terminal of the battery, and causing a motor gear, which is rotatably provided on an upper side of the body housing, to rotate; and a control board provided in the internal space of the body housing, electrically connected to the electric motor and the battery, and controlling a power output of the battery based on a signal input through the operation button to control operations of the electric motor and the cartridge portion.

3. The lifting beauty device using the high-intensity focused ultrasound of claim 2, further comprising:

a coupling portion which is formed on the upper side of the body housing and into which a lower end of the cartridge portion is inserted; and a pair of connection terminals which are spaced apart from the motor gear located at an inner center of the coupling portion by a certain distance and are electrically connected to the control board, and from which power is output to the cartridge portion through the control board.

4. The lifting beauty device using the high-intensity focused ultrasound of claim 3, wherein the cartridge portion includes:

a cartridge housing having an internal space, including an insertion portion inserted into the coupling portion, and having an oval-shaped opening formed in an upper side through which the ultrasonic oscillation head is movable;

a rotational power transfer means accommodated on a lower side inside the cartridge housing and receiving and outputting the rotational power generated by the body portion;

a head transport means mechanically connected to the rotational power transfer means in the internal space of the cartridge housing and linearly transporting the head module with the rotational power output from the rotational power transfer means; and the head module connected to the head transport means in the internal space of the cartridge housing and emitting the high-intensity focused ultrasound (HIFU) while linearly moving by the head transport means.

5. The lifting beauty device using the high-intensity focused ultrasound of claim 4, wherein the rotational power transfer means includes:

a connection gear that is engaged with the motor gear; and a first bevel gear connected to the connection gear by an axis to rotate in conjunction with a rotation of the connection gear.

6. The lifting beauty device using the high-intensity focused ultrasound of claim 5, wherein the head transport means includes:

a rotation shaft having a second bevel gear, which is engaged perpendicularly with the first bevel gear, on one side and having a first spur gear on an opposite side of the one side; and the transfer screw having a length that is parallel to a rotation axis of the rotation shaft and a screw thread formed in the length, and having a second spur gear, which is engaged with the first spur gear, on another side.

7. The lifting beauty device using the high-intensity focused ultrasound of claim 1, wherein the track groove of the guide plate includes:

a first high-intensity focused ultrasound emission section that limits an emission depth of the focused ultrasound to 3.0 mm;

a second high-intensity focused ultrasound emission section that limits the emission depth of the focused ultrasound to 4.5 mm; and a pair of emission depth switching sections connecting one side and another side of the first high-intensity focused ultrasound emission section respectively to one side and another side of the second high-intensity focused ultrasound emission section.

* * * * *